(12) United States Patent
Sato et al.

(10) Patent No.: US 7,790,909 B2
(45) Date of Patent: Sep. 7, 2010

(54) DIOXOLANE DERIVATIVE AND METHOD FOR PRODUCING SAME

(75) Inventors: Haruhito Sato, Chiba (JP); Takuji Okamoto, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 666 days.

(21) Appl. No.: 11/575,255

(22) PCT Filed: Sep. 12, 2005

(86) PCT No.: PCT/JP2005/016780

§ 371 (c)(1),
(2), (4) Date: Mar. 14, 2007

(87) PCT Pub. No.: WO2006/030747

PCT Pub. Date: Mar. 23, 2006

(65) Prior Publication Data

US 2008/0051588 A1    Feb. 28, 2008

(30) Foreign Application Priority Data

Sep. 15, 2004    (JP)    .............................. 2004-268465

(51) Int. Cl.
*C07D 317/12*    (2006.01)
(52) U.S. Cl. .................................... 549/430
(58) Field of Classification Search .................. 549/430
See application file for complete search history.

(56) References Cited

U.S. PATENT DOCUMENTS 4,792,411 A    12/1988    Walsh

FOREIGN PATENT DOCUMENTS

| CS | 211412 | 2/1982 |
|---|---|---|
| CS | 212128 | 2/1982 |
| JP | 1 501867 | 6/1989 |

OTHER PUBLICATIONS

Malik, L. et al.,"Some Conversions of Isometric Epoxyoctanes in Acidic Medium I-Analysis of Reaction Products", Rope a Uhlie, vol. 25, No. 9, pp. 530-543, 1983.
Bulai, A. et al.,"Synthesis of Unsaturated Polyesters from Maleic Anhydrite and Isobutylene Oxide". Vysokomolekulyarnye Soedineniya, Seriya A, vol. 30, No. 8, pp. 1766-1770, 1988.
Yamashita, Y. et al., "Cationic Oligomarization of Isobutylene Oxide", Polymer Bulletin, vol. 1, No. 1, pp. 73-77, 1978.
Wuensch, B. "A New Method for the Preparation of 3-alkoxy- and 3-Hydroxy-3, 4-dihydro-1H-2-benzopyrans", Archiv der Pharmazie, vol. 323, No. 8, pp. 493-499, 1990.
Zhao, H. "Total Synthesis of Cembrene C", Chinese Science Bulletin, vol. 35, No. 23, pp. 2020-2021, 1990.
Mao, J. et al.,"Studies on Macrocyclic Diterpenoids (III) Total Synthesis of Cembrene-C", Science in China, vol. 35, No. 3, pp. 257-261, 1992.
Hearne, G. et al.,"Derivatives of Allylic Chlorides- Reactions of Methallyl Alcohol", Journal of Industrial and Engineering Chemistry, vol. 33. No. 6, pp. 805-809, 1941.
Okada, M et al.,"Polymerizability of Methyl Substituted 1,3-Dioxolanes", Die Macromolekulare Chemie, vol. 176, No. 4, pp. 859-872, 1975.
Eliel, E. et al.,"Carbon-13 NMR Spectra of Saturated Heterocycles-VIII Tetrahydrofurans and 1,3-Dioxolanes", Oroanic Magnetic Resonance, vol. 12, No. 8, pp. 451-466, 1979.
Graham, A. et al.,"Oxidation Products of Diisobutylene- Part III Products from Ring Opening of 1, 2-epoxy-2,4,4-trimetylpentane", Journal of the Chemical Society Abstracts, pp. 2180-2200, 1954.
Sheehan, J. et al.,"The Synthesis and Resolution of Methylleucines", Journal of Organic Chemistry, vol. 28, No. 9, pp. 2279-2282, 1963.
Martin Mugdan, et al., "Catalytic Hydroxylation of Unsaturated Compounds", Journal of the Chemical Society, XP009116854, Aug. 3, 1949, pp. 2988-3000.
B. N. Blackett, et al., "Stereoselectivity in the Boron Trifluoride Catalyzed Rearrangement of a 1, 1-Disubstituted Ethylene Oxide", Journal of the American Chemical Society, vol. 92, No. 8, XP002527633, Apr. 22, 1970, pp. 2574-2575.
U.S. Appl. No. 12/421,428, filed Apr. 9, 2009, Sato et al.

*Primary Examiner*—Taofiq A Solola
(74) *Attorney, Agent, or Firm*—Oblon, Spivak, McClelland, Maier & Neustadt, L.L.P.

(57) ABSTRACT

Provided are a novel compound which improves the solubility of any one of various lubricating oil additives when used as base oil, in particular, a base oil component in a lubricating oil composition, and is capable of realizing low viscosity/low volatility characteristics that have not been achieved in PAO compositions to which conventional additives are added, and a method for producing the compound. Disclosed is 2-alkyl-4,4-dialkyl-1,3-dioxolane having a structure represented by the general formula (I) below: wherein $R^1$ to $R^4$ each independently represent an alkyl group having 1 to 30 carbon atoms.

(I)

$$\begin{array}{c} R^1 \\ \diagdown \\ HC-CH \\ \diagup \\ R^2 \end{array} \begin{array}{c} R^3 \\ | \diagup R^4 \\ O-C \\ | \\ O-CH_2 \end{array}$$

20 Claims, 3 Drawing Sheets

DIOXOLANE DERIVATIVE AND METHOD FOR PRODUCING SAME

TECHNICAL FIELD

The present invention relates to a 2-alkyl-4,4-dialkyl-1,3-dioxolane suitable as a compounding ingredient for use in the fields of a lubricating oil composition, a heating medium, hydraulic oil, and the like, and a method for producing the same.

BACKGROUND ART

Various lubricating oil additives each show low solubility in a synthetic hydrocarbon compound (synthetic base oil) which is obtained by turning 1-decene (linear α-olefin having 10 carbon atoms) into an oligomer and which is referred to as a poly-α-olefin (PAO). In view of the foregoing the solubility is improved by adding a dicarboxylic acid diester (such as diisononyl adipate) at a content of 20 to 40 mass % with respect to the PAO upon use of the PAO. An oligodecene which is obtained by turning 1-decene into an oligomer by using a metallocene catalyst and which has a number average molecular weight of 500 to 200,000 has been disclosed as an example of the PAO (see, for example, Patent Document 1).

A lubricating oil composition has been conventionally prepared by adding any one of various lubricating oil additives to base oil. However, the dissolution of any one of those additives in the base oil requires an increase in polarity. When the oligodecene described in Patent Document 1 described above is used as base oil, and an additive is added to the oligodecene, the sufficient dissolution of the additive in the base oil requires the blending of expensive diisononyl adipate at a content of 30 mass % or more with respect to the oligodecene.

Patent Document 1: Japanese Patent Translation Publication No. 2002-518582

DISCLOSURE OF THE INVENTION

Problems to be Solved by the Invention

The present invention has been made in view of the above circumstances and an object of the present invention is to provide a novel compound which: improves the solubility of any one of various lubricating oil additives when used as base oil, in particular, a base oil component in a lubricating oil composition; and is capable of realizing low viscosity/low volatility characteristics that have not been achieved in a PAO composition to which a conventional additive is added, and a method for producing the compound.

Means for Solving the Problems

The inventors of the present invention have made extensive studies with a view to achieving the above object. As a result, they have found that the solubility of any one of various lubricating oil additives can be improved by introducing oxygen in an ether form into the structure of a PAO so that a polar unit is applied. Further, they have found the following: in the compound, when the ether is of a ring structures molecular weights are uniformized, and a molecular structure is stabilized, whereby characteristics needed for the applications of a lubricating oil composition and a heating medium (a low viscosity is kept and volatility is suppressed) are secured. The present invention has been completed on the basis of such findings.

That is, according to the present invention there are provided the following 2-alkyl-4,4-dialkyl-1,3-dioxolanes and methods for producing the same.

1. A 2-alkyl-4,4-dialkyl-1,3-dioxolane characterized by including a structure represented by the following general formula (I):

[Formula 1]

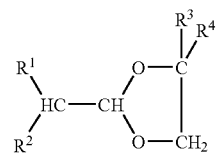

(I)

wherein $R^1$ to $R^4$ each independently represent an alkyl group having 1 to 30 carbon atoms.

2. A 2-alkyl-4,4-dialkyl-1,3-dioxolane according to Item 1, in which the structure represented by the general formula (I) includes a structure represented by the following general formula (II)

[Formula 2]

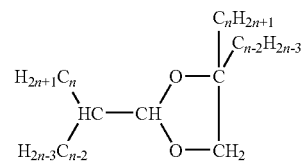

(II)

wherein n represents an integer of 6 to 30.

3. A method for producing the 2-alkyl-4,4-dialkyl-1,3-dioxolane described in Item 1, characterized by including causing a 2-alkylalkane-1,2-epoxide represented by the following general formula (III):

[Formula 3]

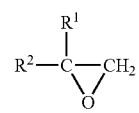

(III)

wherein $R^1$ and $R^2$ each independently represent an alkyl group having 1 to 30 carbon atoms, and a 2-alkylalkane-1,2-diol represented by the following general formula (IV):

[Formula 4]

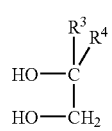

(IV)

wherein $R^3$ and $R^4$ each independently represent an alkyl group having 1 to 30 carbon atoms to react with each other.

4. A method for producing the 2-alkyl-4,4-dialkyl-1,3-dioxolane according to Item 3, in which, in the general formulae (III) and (IV), $R^1$ and $R^3$ each represent $C_nH_{2n+1}$, and $R^2$ and $R^4$ each represent $C_{n-2}H_{2n-3}$ wherein n represents an integer of 6 to 30.

5. A method for producing the 2-alkyl-4,4-dialkyl-1,3-dioxolane described in Item 1, characterized by including causing a 2-alkylalkanal represented by the following general formula (V)

[Formula 5]

(V)

wherein $R^1$ and $R^2$ each independently represent an alkyl group having 1 to 30 carbon atoms, and a 2-alkylalkane-1,2-diol represented by the following general formula (IV):

[Formula 6]

(IV)

wherein $R^3$ and $R^4$ each independently represent an alkyl group having 1 to 30 carbon atoms to react with each other.

6. A method for producing the 2-alkyl-4,4-dialkyl-1,3-dioxolane according to Item 5, in which, in the general formulae (V) and (IV), $R^1$ and $R^3$ each represent $C_nH_{2n+1}$, and $R^2$ and $R^4$ each represent $C_{n-2}H_{2n-3}$ wherein n represents an integer of 6 to 30.

7. A method for producing a 2-alkyl-4,4-dialkyl-1,3-dioxolane represented by the following general formula (I-a), characterized by including subjecting a 2-alkylalkane-1,2-diol represented by the following general formula (IV) to a dehydration dimerization reaction:

[Formula 7]

(IV)

wherein $R^3$ and $R^4$ each independently represent an alkyl group having 1 to 30 carbon atoms;

[Formula 8]

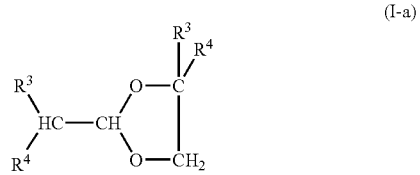

(I-a)

wherein $R^3$ and $R^4$ each have the same meaning as that described above.

8. A method for producing the 2-alkyl-4,4-dialkyl-1,3-dioxolane according to Item 7, in which, in the general formulae (IV) and (I-a), $R^3$ represents $C_nH_{2n+1}$, and $R^4$ represents $C_{n-2}H_{2n-3}$ wherein n represents an integer of 6 to 30.

9. A lubricating oil composition, including the 2-alkyl-4,4-dialkyl-1,3-dioxolane described in Item 1 or 2.

10. A heating medium, including the 2-alkyl-4,4-dialkyl-1,3-dioxolane described in Item 1 or 2.

EFFECT OF THE INVENTION

The use of each of the 2-alkyl-4,4-dialkyl-1,3-dioxolanes of the present invention as a component in base oil can provide a lubricating oil composition or hydraulic oil which: improves the solubility of any one of various lubricating oil additives to be added to the base oil; and is suitable for various applications. In addition, the 2-alkyl-4,4-dialkyl-1,3-dioxolane can be used also as a base oil component in a heating medium.

BEST MODE FOR CARRYING OUT THE INVENTION

Figure 1:
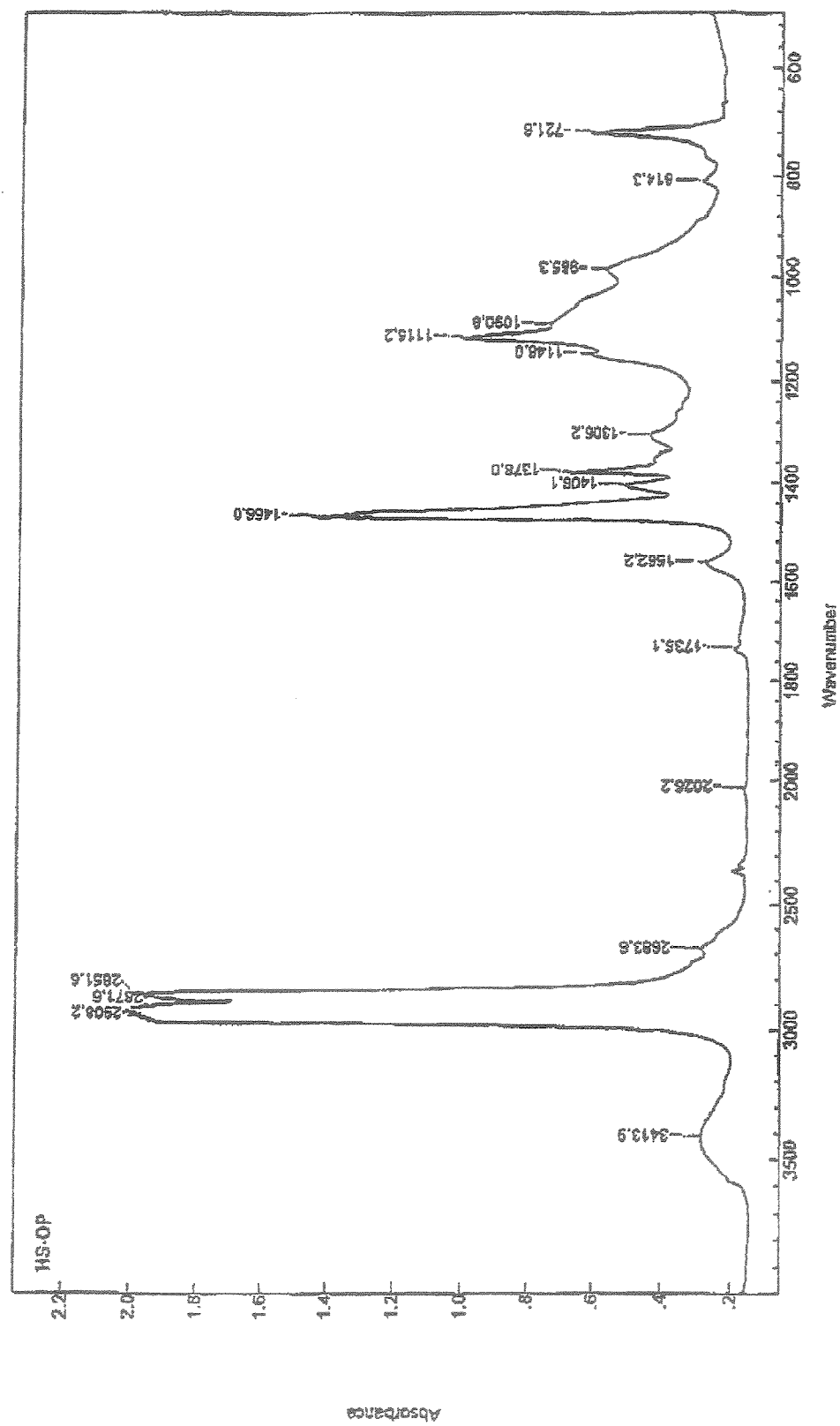
FIG. 1 A chart showing an infrared absorption spectrum in the detailed analysis of 2-(n-nonadecanyl-9)-4-octyl-4-decyl-1,3-dioxolane.

A 2-alkyl-4,4-dialkyl-1,3-dioxolane of the present invention is a novel compound not described in any documents and has a structure represented by the following general formula (I)

[Formula 9]

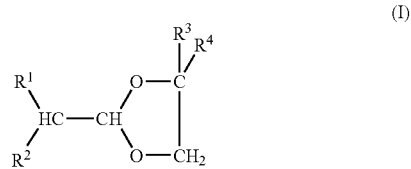

(I)

In the formula, $R^1$ to $R^4$ each independently represent an alkyl group having 1 to 30 carbon atoms. The alkyl group may be linear, branched, or cyclic, and specific examples of the alkyl group include methyl group, an ethyl group, various propyl groups, various butyl groups, various pentyl groups, various hexyl groups, various heptyl groups, various octyl groups, various nonyl groups, various decyl groups, various dodecyl groups, various tetradecyl groups, a cyclopentyl group, and a cyclohexyl group A preferable example of the 2-alkyl-4,4-dialkyl-1,3-dioxolane represented by the above general formula (I) is a 2-alkyl-4,4-dialkyl-1,3-dioxolane represented by the following general formula (II):

[Formula 10]

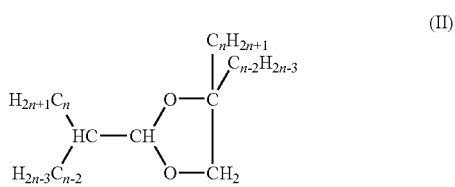

(II)

wherein n represents an integer of 6 to 30. A compound represented by the above general formula (II) in which $C_nH_{2n+1}$ and $C_{n-2}H_{2n-3}$ each represent a linear alkyl group is more preferable. n described above preferably represents an integer of 8 to 22.

Although a method for producing the 2-alkyl-4,4-dialkyl-1,3-dioxolane represented by the above general formula (I) is not particularly limited, the above 2-alkyl-4,4-dialkyl-1,3-dioxolane can be efficiently produced in accordance with a method of the present invention to be described below.

There are three modes of the method for producing the 2-alkyl-4,4-dialkyl-1,3-dioxolane of the present invention. First, a 2-alkylalkane-1,2-epoxide, a 2-alkylalkane-1,2-diol, and a 2-alkylalkanal as raw materials for use in those modes will be described.

Each of the 2-alkylalkane-1,2-epoxide and the 2-alkylalkane-1,2-diol can be synthesized by using a 1-olefin dimer as a raw material. The 1-olefin dimer can be synthesized by using a metallocene complex/an organic aluminum compound, a metallocene complex/a borate compound, or a metallocene complex/an organic aluminum compound/a borate compound as a catalyst. Examples of the metallocene complex include complexes of metals belonging to Group 4 in the periodic table each having a carbon conjugated five-membered ring structure such as zirconocene dichloride, bis(dimethylcyclopentadienyl)zirconium dichloride, bis(indenyl zirconium dichloride, and bis(tetrahydroindenyl)zirconium dichloride Those each obtained by: replacing "zirconium" in each of those metal complexes with "titanium" or "hafnium"; or replacing "chloride" in each of those metal complexes with "alkyl", "1,3-diketone", "β-ketoester", or "trifluoromethanesulfonate" can also be used.

Examples of the organic aluminum compound include methylalumoxane, isobutylalumoxane, triethyl aluminum, triisobutyl aluminum, and trioctyl aluminum Examples of the borate compound include tetraphenylborate triethylammonium, tetraphenylborate tri-n-butylammonium, tetraphenylborate trimethylammonium, tetraphenylborate tetraethylammonium, and tetrakis(pentafluorophenyl)borate dimethylanilinium.

A dimerization reaction can be performed by: sequentially adding a catalyst and a 1-olefin to a hydrocarbon solvent; and stirring the mixture at a temperature of typically 120° C. or lower, or preferably 20 to 80° C. for 8 to 40 hours. After the reaction, the mixture is deactivated with hydrogen chloride water, and the product is distilled in a vacuum, whereby a dimerized product having a high purity can be obtained in high yield.

The 2-alkylalkane-1,2-epoxide can be synthesized by: mixing the olefin dimer (vinylidene type) obtained in the foregoing and hydrogen peroxide at a charge molar ratio of hydrogen peroxide to the dimer of 1 or more; and subjecting the mixture to an epoxidation reaction. An aqueous solution of hydrogen peroxide having a hydrogen peroxide content of 20 to 80 mass % is used as hydrogen peroxide. An inorganic acid such as sulfuric acid is added in a small amount (at a molar ratio of the inorganic acid to the dimer of less than 1) to the two-layer mixture of the olefin dimer and the aqueous solution of hydrogen peroxide, and the mixture is stirred at a temperature of about 60 to 100° C. for about 2 to 12 hours. After that, the water layer as a lower layer is removed, and an aqueous solution of hydrogen peroxide similar to that described above and a small amount of an inorganic acid such as sulfuric acid are added to the remainder. Subsequently the mixture is stirred at a temperature of about 60 to 1000° C. for about 2 to 12 hours. After the reaction, an upper layer is taken out and washed with an alkali, whereby the 2-alkylalkane-1, 2-epoxide is obtained.

The 2-alkylalkane-1,2-diol can be synthesized by: mixing the olefin dimer (vinylidene type) obtained in the foregoing, hydrogen peroxide, and formic acid at a charge molar ratio of hydrogen peroxide to the dimer of 1 or more and at a charge molar ratio of formic acid to the dimer of 1 or more; and subjecting the mixture to a dihydroxylation reaction. An aqueous solution of hydrogen peroxide having a hydrogen peroxide content of 20 to 80 mass % is used as hydrogen peroxide. The aqueous solution of hydrogen peroxide is added to the mixed solution of the olefin dimer and formic acids and the mixture is stirred at a temperature of about 20 to 50° C. for about 2 to 24 hours. After that an aqueous solution of hydrogen peroxide similar to that described above is added, and the mixture is stirred at a temperature of about 20 to 50° C. for about 2 to 24 hours. After the reaction, formic acid is removed by distillation from the product. The remainder is treated with an alkali, and is then distilled in a vacuum, whereby the 2-alkylalkane-1,2-diol is obtained.

The 2-alkylalkanal can be obtained by subjecting a 2-alkylalkanol to an oxidation reaction. For example, chromium (VI) oxide is used as an oxidant, and the mixture of a 2-alkylalkanol and chromium (VI) oxide at a charge molar ratio of the 2-alkylalkanol to chromium (VI) oxide of 1/0.2 to 1/2 is stirred at about 20 to 80° C. for about 4 to 48 hours. After that, unreacted dichromium trioxide is separated by filtration, and the produced liquid is purified with a column, whereby the 2-alkylalkanal is obtained.

Next, a first mode of the method for producing the 2-alkyl-4,4-dialkyl-1,3-dioxolane will be described. In the first mode in the production method of the present invention, a 2-alkylalkane-1,2-epoxide represented by the following general formula (III):

[Formula 11]

(III)

wherein $R^1$ and $R^2$ each independently represent an alkyl group having 1 to 30 carbon atoms, and a 2-alkylalkane-1,2-diol represented by the following general formula (IV):

[Formula 12]

(IV)

wherein $R^3$ and $R^4$ each independently represent an alkyl group having 1 to 30 carbon atoms are caused to react with each other. As a result of the reaction, the 2-alkyl-4,4-dialkyl-3-dioxolane represented by the above general formula (II is produced.

In a second mode, a 2-alkylalkanal represented by the following general formula (V)

[Formula 13]

(V)

wherein $R^1$ and $R^2$ each independently represent an alkyl group having 1 to 30 carbon atoms, and a 2-alkylalkane-1,2-diol represented by the following general formula (IV):

[Formula 14]

(IV)

wherein $R^3$ and $R^4$ each Independently represent an alkyl group having 1 to 30 carbon atoms are caused to react with each other. As a result of the reaction, the 2-alkyl-4,4-dialkyl-1,3-dioxolane represented by the above general formula (I) is produced.

In a third mode, the 2-alkylalkane-1,2-diol represented by the above general formula (IV) is subjected to a dehydration dimerization reaction to produce a 2-alkyl-4,4-dialkyl-1,3-dioxolane represented by the following general formula (I-a):

[Formula 15]

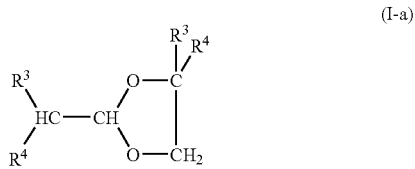

(I-a)

wherein $R^3$ and $R^4$ each have the same meaning as that described above.

Raw materials represented by the above general formulae (III), (IV), and (V) in which $R^1$ and $R^3$ each represent $C_nH_{2n+1}$, and $R^2$ and $R^4$ each represent $C_{n-2}H_{2n-3}$ are preferable in the above production method. n represents an integer of 6 to 30, or preferably represents an integer of 8 to 22.

In the case of the above first mode, the reaction between the 2-alkylalkane-1,2-epoxide represented by the above general formula (III) and the 2-alkylalkane-1,2-diol represented by the above general formula (IV) is performed at a temperature of typically about 60 to 200° C., or preferably 80 to 180° C. In additions a time period for the reaction is typically about 1 to 24 hours, or preferably 2 to 12 hours.

In the case of the above second mode, the reaction between the 2-alkylalkanal represented by the above general formula (V) and the 2-alkylalkane-1,2-diol represented by the above general formula (IV) is performed at a temperature of typically about 60 to 180° C., or preferably 80 to 160° C. In addition, a time period for the reaction is typically about 1 to 12 hours, or preferably 2 to 8 hours.

In the case of the above third mode, the dehydration dimerization reaction of the 2-alkylalkane-1,2-diol represented by the above general formula (IV) is performed at a temperature of typically about 60 to 200° C., or preferably 80 to 180° C. In addition, a time period for the reaction is typically about 1 to 24 hours, or preferably 2 to 12 hours.

In the case of the above second mode, Guerbet aldehyde synthesized by subjecting Guerbet alcohol to an oxidation treatment with an oxidant such as chromium oxide, or an aldehyde synthesized from the above epoxide is preferable as the 2-alkylalkanal represented by the above general formula (V).

The use of the 2-alkyl-4,4-dialkyl-1,3-dioxolane of the present invention as a component in base oil, in particular, base oil of lubricating oil can provide a composition which: improves the solubility of any one of various lubricating oil additives; is capable of realizing low viscosity/low volatility characteristics; and is suitable as a lubricating oil composition. In addition, the 2-alkyl-4,4-dialkyl-1,3-dioxolane can be used also as a base oil component in a heating medium. In this case, among all kinds of the 2-alkyl-4,4-dialkyl-1,3-dioxolane of the present invention, the 2-alkyl-4,4-dialkyl-1,3-dioxolane represented by the above general formula (II) is preferable, and a compound represented by the above general formula (II) in which $C_nH_{2n+1}$ and $C_{n-2}H_{2n-3}$ each represent a linear alkyl group is more preferable. In the case of a lubricating oil composition, mineral oil or synthetic oil can be used as base oil in combination. The mineral oil or the synthetic oil is not particularly limited as long as it is generally used as base oil of lubricating oil.

There are various kinds of such mineral oil and synthetic oil, and it is sufficient that an appropriate one be selected depending on, for example, applications Examples of the mineral oil include a paraffin base mineral oil, a naphthene base mineral oil, and an intermediate base mineral oil. Specific examples of the mineral oil include a light neutral oil, a medium neutral oil, a heavy neutral oil, and a bright stock each obtained by solvent refining or hydrogenation refining.

On the other hand, examples of the synthetic oil include an α-olefin copolymer, polybutene, polyisobutylene, a water-insoluble polyalkylene glycol, an alkylbenzene, a polyol ester, a dibasic acid ester, a polyoxyalkylene glycol, a polyoxyalkylene glycol ester; a polyoxyalkylene glycol ether; a hindered ester; and silicone oil. One kind of those base oils can be used alone, or two or more kinds of them can be used in combination. Mineral oil and synthetic oil may be used in combination.

The load of the 2-alkyl-4,4-dialkyl-1,3-dioxolane of the present invention in a lubricating oil composition or a heating medium is typically 20 mass % or more, or preferably 40 mass % or more on the basis of the composition or the heating medium.

In ordinary cases, known additives such as a stabilizer, an oiliness improver an extreme pressure agent, a dispersant a corrosion inhibitor an antioxidant, and a defoaming agent can be appropriately added to the lubricating oil composition for maintaining the basic performance of the composition as a lubricating oil agent to the extent that an effect of the present invention is not inhibited. The total addition amount of those additives is typically in the range of 0.01 to 20 mass % on the basis of the composition.

EXAMPLES

Next, the present invention will be described in more detail by way of examples. However, the present invention is not limited by these examples at all.

Example 1

Synthesis of 2-(n-nonadecanyl-9)-4-octyl-4-decyl-1,3-dioxolane 2-(n-nonadecanyl-9)-4-octyl-4-decyl-1,3-dioxolane was synthesized Through the following synthesis pathway.

[Formula 16]

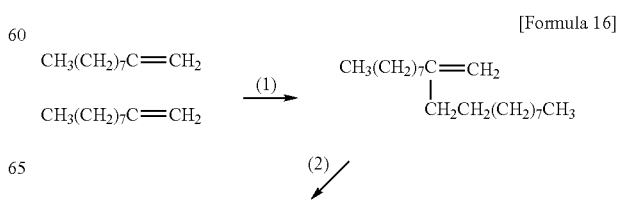

-continued

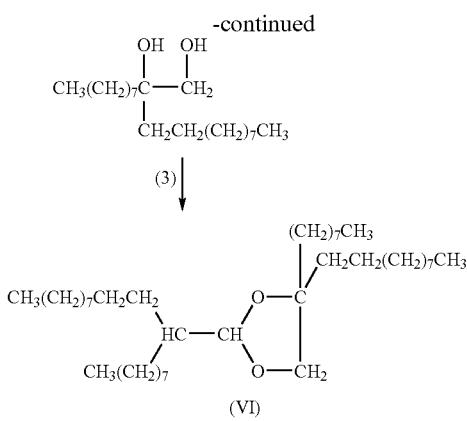

(1) Synthesis of 2-octyl-1-dodecene 3.0 kg of 1-decene, 0.9 g (3 mmol) of zirconocene dichloride as a metallocene complex, and methylalumoxane (manufactured by Albemarle Corporation, 8 mmol in terms of Al) were sequentially added to a three-necked flask having an internal volume of 5 L and replaced with nitrogen and the whole was stirred at room temperature (about 20° C.). The color of the reaction liquid changed from yellow to reddish brown. After a lapse of 48 hours from the initiation of the reaction, the reaction was stopped with methanol. Subsequently, an aqueous solution of hydrochloric acid having a concentration of 2 mass % was added to the reaction liquid to wash an organic layer. Next, the organic layer was distilled in a vacuum, whereby 2.5 kg of a fraction (decene dimer) having a boiling point of 120 to 125° C./26.7 Pa (0.2 Torr) were obtained. The analysis of the fraction by means of gas chromatography confirmed that the concentration of the dimer was 99 mass % and the ratio of a vinylidene olefin in the dimer was 97 mass %.

(2) Synthesis of 2-octyldodecane-1,2-diol 70 g (0.25 mol) of the decene dimer synthesized in the above item (1) and 300 ml of formic acid were added to a three-necked flask having an internal volume of 500 ml. While the resultant mixture was stirred at room temperature, 35 g (0.31 mol) of 30-mass % hydrogen peroxide water were added, and then the whole was stirred for 12 hours with its temperature kept at 40° C. After that, 7 g (0.06 mol) of 30-mass % hydrogen peroxide water were further added to the resultant, and the whole was continuously stirred again for 12 hours. After the reaction, formic acid was removed by distillation under reduced pressure by using a rotary evaporator. Next, a solution prepared by dissolving NaOH in ethanol was added to the remainder, and the whole was subjected to a reflux treatment for 1 hour. Then, ethanol was removed, and the remainder was neutralized. After that, an organic layer was distilled in a vacuum, whereby 57 g of a fraction having a boiling point of 154 to 159° C./26.7 Pa (0.2 Torr) were obtained 72% yield). The analysis of the fraction by means of gas chromatography confirmed that the purity of 2-octyldodecane-1,2-diol was 95%.

(3) Synthesis of 2-(n-nonadecanyl-9)-4-octyl-4-decyl-1,3-dioxolane 1 g of a 0.1-mass % aqueous solution of sulfuric acid was added to 100 g of 2-octyldodecane-1,2-diol synthesized in the item (2), and the whole was heated while being stirred. Then, the mixture was heated for 3 hours with its temperature kept at 150° C. After that, the reaction liquid was cooled and diluted with hexane, whereby a diluted liquid was obtained. Next, the diluted liquid was washed with an aqueous solution of sodium carbonate, and an oil layer was separated. After that, hexane was removed by distillation by using an evaporator. The temperature of the residual liquid thus obtained was heated to 200° C. under reduced pressure (13.3 Pa (0.1 Torr)), whereby a volatile fraction was removed. Thus, 85 g of 2-(n-nonadecanyl-9)-4-octyl-4-decyl-1,3-dioxolane were obtained (89% yield).

(4) Structural analysis of 2-(n-nonadecanyl-9)-4-octyl-4-decyl-1,3-dioxolane

Figure 2:
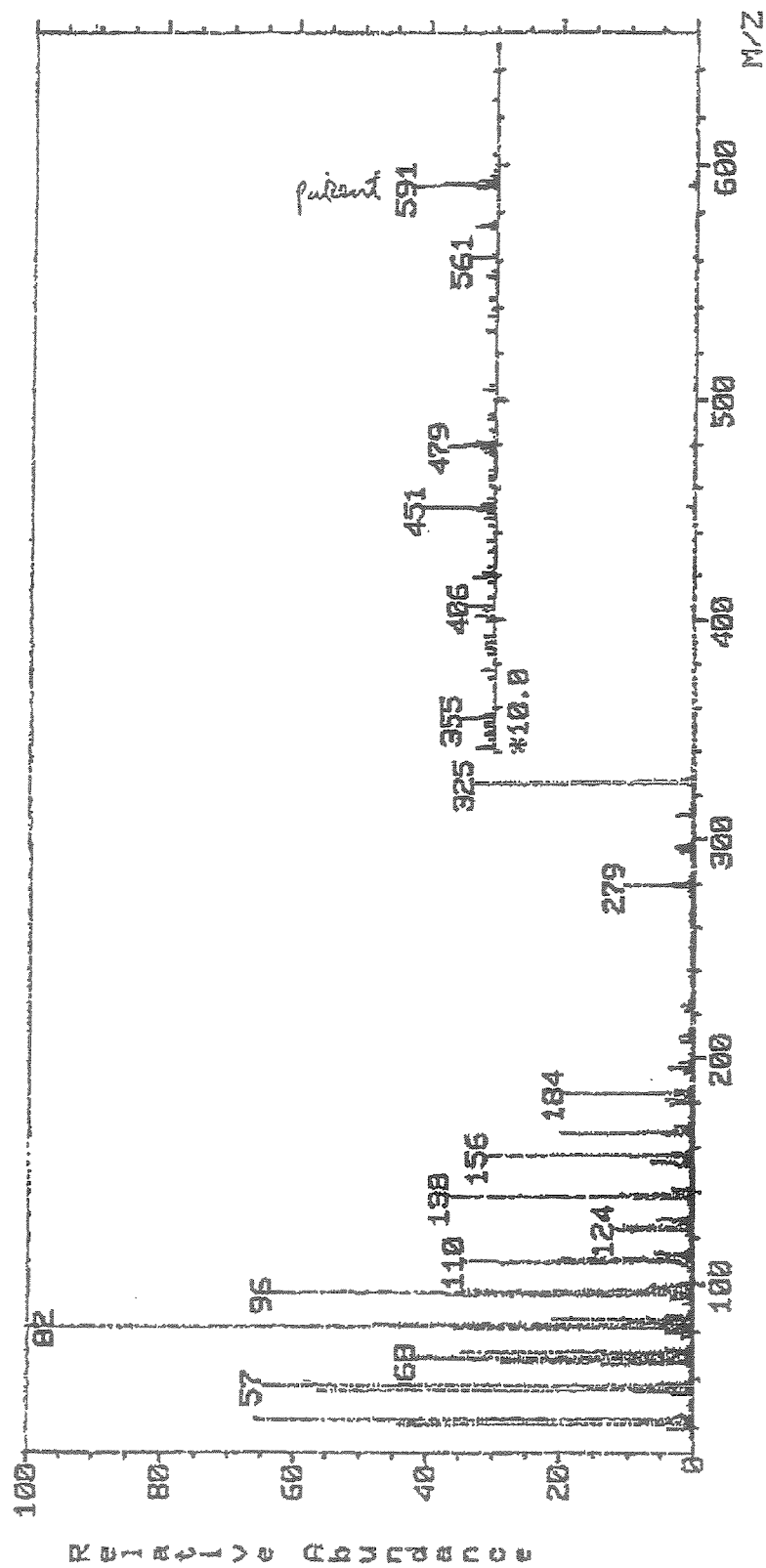
FIG. 2 A chart showing a mass spectrum in the detailed analysis of 2-(n-nonadecanyl-9)-4-octyl-4-decyl-1,3-dioxolane.

The structure of 2-(n-nonadecanyl-9)-4-octyl-4-decyl-1,3-dioxolane synthesized in the above item (3) was identified by using an infrared absorption spectrum (IR: FIG. 1) and a mass spectrum based on gas chromatography (MAS: FIG. 2). The IR analysis resulted in the appearance of an anti-symmetric stretching $v_{R-O-R}=115$ cm$^{-1}$ showing the characteristic absorption of ether, and the MAS analysis resulted in a parent peak 391 ($C_{40}H_{80}O_2=592$), a fragment 325 ($C_{21}H_{42}O_2=326$), and a fragment 279 ($C_{20}H_{40}=280$) supporting a d-oxolane structure. In additions measurement by means of gel permeation chromatography (GPC) confirmed that no oligomer component having a molecular weight higher than that of 2-(n-nonadecanyl-9)-4-octyl-4-decyl-1,3-dioxolane was incorporated.

Figure 3:
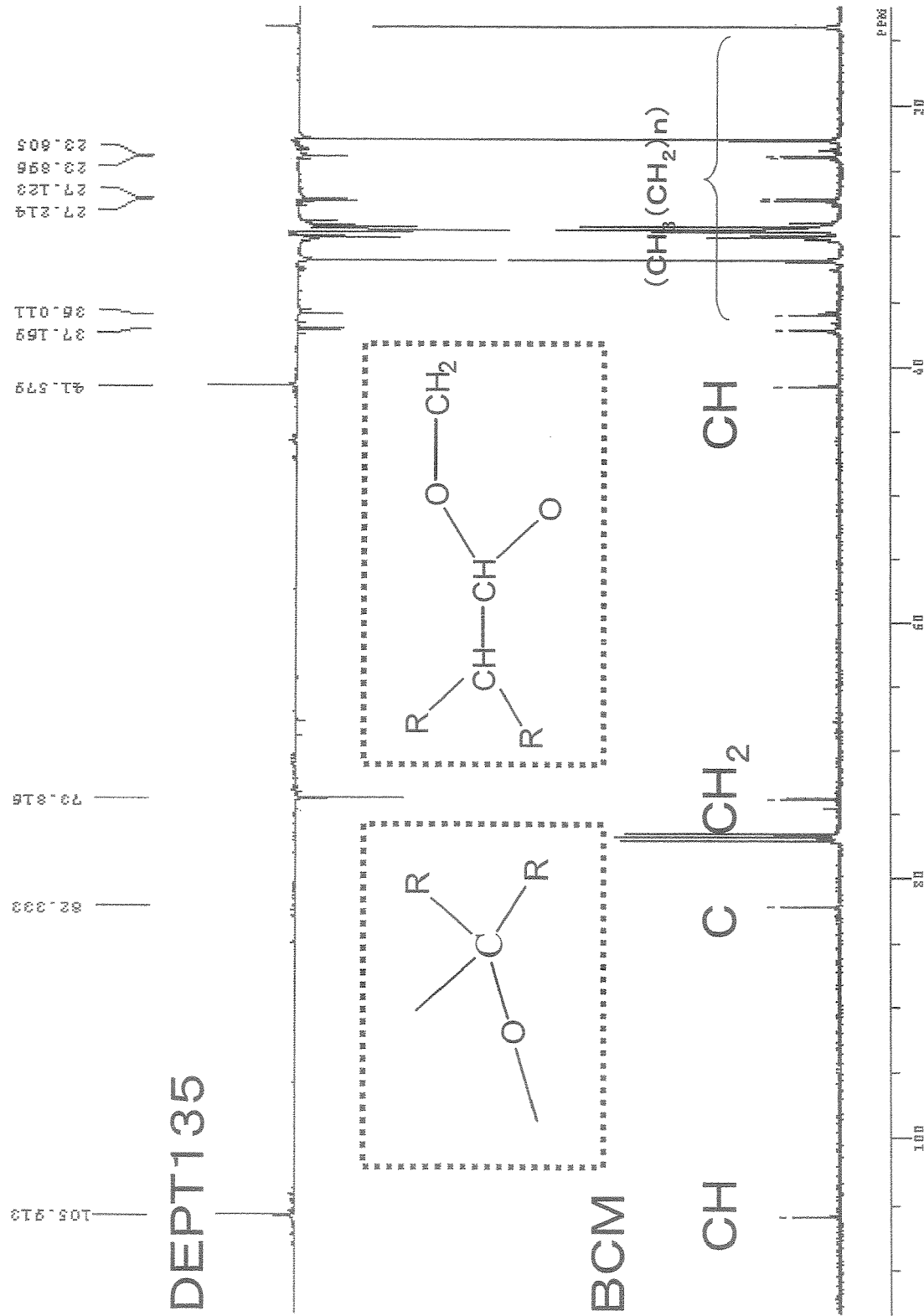
FIG. 3 A chart showing a $^{13}$C-NMR data profile in the detailed analysis of 2-(n-nonadecanyl-9)-4-octyl-4-decyl-1,3-dioxolane.

Next, analysis using $^{13}$C-NMR (FIG. 3) confirmed that this compound had a 1,3-dioxolane structure. The upper stage of FIG. 3 represents the measurement chart of distortion less enhancement by polarization transfer (DEPT), and the lower stage of FIG. 3 represents the measurement chart of bilevel complete decoupling (BCM). The analysis of the charts showed that this compound had one quaternary carbon atom, two tertiary carbon atoms (CH), and one secondary carbon atom which was present near a polar group. The integration of the analysis based on $^{13}$C-NMR, the above IR analysis, and the above MAS analysis identified the structure of this compound as the structure of 2-(n-nonadecanyl-9)-4-octyl-4-decyl-1,3-dioxolane represented by the above formula (VI) in which 2-position was an unbranched isoalkyl group and 4-position was a linear alkyl group.

(5) Basic physical properties of 2-(n-nonadecanyl-9)-4-octyl-4-decyl-1,3-dioxolane The viscosities of 2-(n-nonadecanyl-9)-4-octyl-4-decyl-1,3-dioxolane synthesized in the above item (3) were measured at 40° C. and 100° C. in conformance with JIS K 2283. The measurement confirmed that 2-(n-nonadecanyl-9)-4-octyl-4-decyl-1,3-dioxolane had a viscosity of 49.62 mm$^2$/s at 40° C. and a viscosity of 7.55 mm$^2$/s at 100° C. In addition, 20 mg of dioxane were loaded into a beaker having a diameter of 50 mm and a height of 50 mm and the beaker was maintained in a rotating thermostat at 120° C. for 24 hours. After that, the beaker was taken out, and the ratio at which the weight of dioxane reduced was measured. The measurement confirmed that the ratio at which the weight of dioxane reduced owing to evaporation was 5 mass % or less. Those results showed that this dioxane was oil having low volatility and a relatively low viscosity, and had heat resistance.

Example 2

Synthesis of 2-(n-nonadecanyl-9)-4-octyl-4-decyl-1,3-dioxolane (1) Synthesis of 2-octyldodecanal 200 g (0.67 mol) of 2-octyldodecanol [manufactured by Aldrich, reference number 46,448-1] and 23 g of chromium (VI) oxide [manufactured by KANTO KAGAKU reference number 07355-00] were added to a three-necked flask having an internal volume of 1 L. The reaction mixture was stirred at room temperature for 18 hours. The reaction temperature was gradually increased to 60° C. over 2 hours, and stirring was performed at the temperature for 4 hours. After the reaction, solid matter was filtered, and the reaction product was washed with an aqueous solution of sodium hydrogen carbonate and dried. The resultant reactant was distilled under reduced pressure, and 112 g of a fraction having a boiling point of 125 to 135° C. (degree of pressure reduction 13.3 Pa (0.1 Torr)) were collected (56% coarse yield). The analysis of the fraction by means of gas chromatography confirmed that the content of 2-octyldodecanal was 78 mass %.

(2) Synthesis of 2-n-nonadecanyl-9)-4-octyl-4-decyl-1,3-dioxolane 0.2 g of a 0.1-mass % aqueous solution of sulfuric acid was added to the mixture of 50 g of 2-octyldodecanal synthesized in the above item (1) and 50 g of 2-octyldodecane-1,2-diol synthesized in the item (2) of Example 1, and the whole was heated while being stirred. Then, the mixture was heated for 3 hours with its temperature kept at 150° C. After that, the reaction liquid was cooled and diluted with hexane, whereby a diluted liquid was obtained. Next, the diluted liquid was washed with an aqueous solution of sodium carbonate and an oil layer was separated. After that, hexane was removed by distillation by using an evaporator. The temperature of the residual liquid thus obtained was heated to 200° C. under reduced pressure (13.3 Pa (0.1 Torr)), whereby a volatile fraction was removed. Thus, 79 g of 2-(n-nonadecanyl-9)-4-octyl-4-decyl-1,3-dioxolane were obtained (81% yield)

Applied Example 1

Solubility Test for Additive

Each of 0.1 g of zinc dithiophosphate (ZnDTP) (Zn content 9.0 mass %, P content 7.8 mass %), 0.1 g of molybdenum dithiocarbamate (Mo content 4.5 mass %, S content 5.7 mass %) and 0.5 g of a detergent dispersant (manufactured by Lubrizol Corporation, LZ 400) was added to 10 g of 2-(n-nonadecanyl-9)-4-octyl-4-decyl-1,3-dioxolane synthesized in the item (3) of Example 1, and the resultant mixed liquid was stirred at 25° C. for 24 hours. As a result, each of the additives was uniformly dissolved, and nearly transparent oil was obtained.

In addition, a solubility test was performed in the same manner as that described above except that poly-α-olefin (manufactured by Idemitsu Petrochemical Co, Ltd., PAO 5006 (average compositional formula: $C_{40}H_{88}$)) containing no oxygen atom was used instead of 2-(n-nonadeanyl-9)-4-octyl-4-decyl-1,3-dioxolane (compositional formula: $C_{40}H_{84}O_2$). As a result, none of the additives was dissolved, and suspended oil was obtained.

INDUSTRIAL APPLICABILITY

The use of the 2-alkyl-4,4-dialkyl-1,3-dioxolane of the present invention as a component in base oil can provide a composition suitable as a lubricating oil composition or as a heating medium.

The invention claimed is:

1. A 2-alkyl-4,4-dialkyl-1,3-dioxolane derivative represented by the following general formula (I):

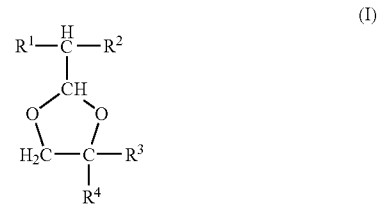

wherein $R^1$, $R^2$, $R^3$ and $R^4$ each independently represent an alkyl group having 4-30 carbon atoms.

2. The 2-alkyl-4,4-dialkyl-1,3-dioxolane derivative according to claim 1, wherein $R^1$, $R^2$, $R^3$ and $R^4$ each independently represent an alkyl group having 8-30 carbon atoms.

3. The 2-alkyl-4,4-dialkyl-1,3-dioxolane derivative according to claim 1, wherein $R^1$, $R^2$, $R^3$ and $R^4$ each independently represent an alkyl group having 9-30 carbon atoms.

4. The 2-alkyl-4,4-dialkyl-1,3-dioxolane derivative according to claim 1, which is represented by the following general formula (II):

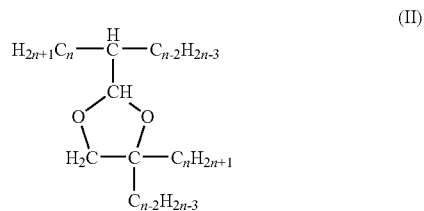

wherein n is an integer of 6-30.

5. The 2-alkyl-4,4-dialkyl-1,3-dioxolane derivative according to claim 4, wherein n is an integer of 10-30.

6. The 2-alkyl-4,4-dialkyl-1,3-dioxolane derivative according to claim 4, wherein n is an integer of 11-30.

7. The 2-alkyl-4,4-dialkyl-1,3-dioxolane derivative according to claim 4, wherein n is an integer of 10.

8. A method for producing the 2-alkyl-4,4-dialkyl-1,3-dioxolane derivative according to claim 1, wherein the method comprises:

reacting a 2-alkylalkane-1,2-epoxide compound represented by the following general

[Formula III]:

wherein $R^1$ and $R^2$ each independently represent an alkyl group having 4-30 carbon atoms, with a 2-alkylalkane-1,2-diol compound represented by the following general

[Formula IV]:

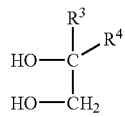

(IV)

wherein $R^3$ and $R^4$ each independently represent an alkyl group having 4-30 carbon atoms.

9. The method for producing the 2-alkyl-4,4-dialkyl-1,3-dioxolane derivative according to claim 8, wherein in the general formulae (III) and (IV), $R^1$ and $R^3$ each represent $C_nH_{2n+1}$, $R^2$ and $R^4$ each represent $C_{n-2}H_{2n-3}$, and n is an integer of 10-30.

10. The method for producing the 2-alkyl-4,4-dialkyl-1,3-dioxolane derivative according to claim 8, wherein in the general formulae (III) and (IV), $R^1$ and $R^3$ each represent $C_nH_{2n+1}$, $R^2$ and $R^4$ each represent $C_{n-2}H_{2n-3}$, and n is an integer of 11-30.

11. A method for producing the 2-alkyl-4,4-dialkyl-1,3-dioxolane derivative according to claim 1, wherein the method comprises:
reacting a 2-alkylalkanal compound represented by the following general

[Formula V]:

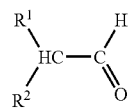

(V)

wherein $R^1$ and $R^2$ each independently represent an alkyl group having 4-30 carbon atoms, with a 2-alkylalkane-1,2-diol compound represented by the following general formula (IV):

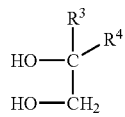

(IV)

wherein $R^3$ and $R^4$ each independently represent an alkyl group having 4-30 carbon atoms.

12. The method for producing the 2-alkyl-4,4-dialkyl-1,3-dioxolane derivative according to claim 11, wherein in the general formulae (IV) and (V), $R^1$ and $R^3$ each represent $C_nH_{2n+1}$, $R^2$ and $R^4$ each represent $C_{n-2}H_{2n-3}$, and n is an integer of 10-30.

13. The method for producing the 2-alkyl-4,4-dialkyl-1,3-dioxolane derivative according to claim 11, wherein in the general formulae (IV) and (V), $R^1$ and $R^3$ each represent $C_nH_{2n-1}$, $R^2$ and $R^4$ each represent $C_{n-2}H_{2n-3}$, and n is an integer of 11-30.

14. A method for producing a 2-alkyl-4,4-dialkyl-1,3-dioxolane derivative represented by the following general formula (I-a):

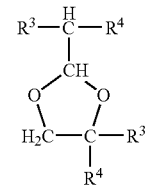

(I-a)

wherein $R^3$ and $R^4$ each independently represent an alkyl group having 4-30 carbon atoms, wherein the method comprises:
subjecting to a dehydration dimerization reaction a 2-alkylalkane-1,2-diol compound represented by the following general formula (IV):

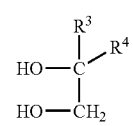

(IV)

wherein $R^3$ and $R^4$ of the general formula (IV) are identical to $R^3$ and $R^4$ of the general formula (I-a).

15. The method for producing the 2-alkyl-4,4-dialkyl-1,3-dioxolane derivative according to claim 14, wherein in the general formulae (I-a) and (IV), $R^3$ represents $C_nH_{2n+1}$, $R^4$ represents $C_{n-2}H_{2n-3}$, and n is an integer of 10-30.

16. The method for producing the 2-alkyl-4,4-dialkyl-1,3-dioxolane derivative according to claim 14, wherein in the general formulae (I-a) and (IV), $R^3$ represents $C_nH_{2n+1}$, $R^4$ represents $C_{n-2}H_{2n-3}$, and n is an integer of 11-30.

17. A composition comprising:
a base oil;
the 2-alkyl-4,4-dialkyl-1,3-dioxolane derivative according to claim 1; and
an optional additive.

18. The composition according to claim 17, wherein the 2-alkyl-4,4-dialkyl-1,3-dioxolane derivative is present in an amount of at least 20 wt. %, based on a total weight of the composition.

19. A composition comprising:
a base oil;
the 2-alkyl-4,4-dialkyl-1,3-dioxolane derivative according to claim 4; and
an optional additive.

20. The composition according to claim 19, wherein the 2-alkyl-4,4-dialkyl-1,3-dioxolane derivative is present in an amount of at least 20 wt. %, based on a total weight of the composition.

* * * * *